United States Patent
Cline et al.

(10) Patent No.: US 6,899,675 B2
(45) Date of Patent: May 31, 2005

(54) FLUORESCENCE ENDOSCOPY VIDEO SYSTEMS WITH NO MOVING PARTS IN THE CAMERA

(75) Inventors: Richard W. Cline, Vancouver (CA); John J. P. Fengler, North Vancouver (CA)

(73) Assignee: Xillix Technologies Corp., Richmond (CA)

( * ) Notice: Subject to any disclaimer, the term of this patent is extended or adjusted under 35 U.S.C. 154(b) by 50 days.

(21) Appl. No.: 10/050,601

(22) Filed: Jan. 15, 2002

(65) Prior Publication Data

US 2003/0135092 A1 Jul. 17, 2003

(51) Int. Cl.[7] .................................................. A61B 1/05
(52) U.S. Cl. ........................................ 600/160; 600/109
(58) Field of Search .......................... 600/109–112, 160, 600/176

(56) References Cited

U.S. PATENT DOCUMENTS

| | | |
|---|---|---|
| 3,971,068 A | 7/1976 | Gerhardt et al. |
| 4,115,812 A | 9/1978 | Akatsu |
| 4,149,190 A | 4/1979 | Wessler et al. |
| 4,200,801 A | 4/1980 | Schuresko |
| 4,378,571 A | 3/1983 | Handy |
| 4,449,535 A * | 5/1984 | Renault ..................... 600/312 |
| 4,532,918 A | 8/1985 | Wheeler |
| 4,556,057 A | 12/1985 | Hiruma et al. |
| 4,638,365 A | 1/1987 | Kato |
| 4,768,513 A | 9/1988 | Suzuki |
| 4,786,813 A | 11/1988 | Svanberg et al. |
| 4,821,117 A | 4/1989 | Sekiguchi |
| 4,837,625 A | 6/1989 | Douziech et al. |
| 4,930,516 A | 6/1990 | Alfano et al. |
| 4,951,135 A | 8/1990 | Sasagawa et al. |
| 4,954,897 A | 9/1990 | Ejima et al. |
| 5,007,408 A | 4/1991 | Ieoka |
| 5,034,888 A | 7/1991 | Uehara et al. |
| 5,134,662 A | 7/1992 | Bacus et al. |
| 5,165,079 A | 11/1992 | Schulz-Hennig |
| 5,214,503 A | 5/1993 | Chiu et al. |
| 5,225,883 A | 7/1993 | Carter et al. |
| 5,255,087 A | 10/1993 | Nakamura et al. |
| 5,365,057 A | 11/1994 | Morley et al. |
| 5,371,355 A | 12/1994 | Wodecki |
| 5,377,686 A | 1/1995 | O'Rourke et al. |
| 5,408,263 A | 4/1995 | Kikuchi et al. |
| 5,410,363 A | 4/1995 | Capen et al. |
| 5,419,323 A | 5/1995 | Kittrell et al. |
| 5,420,628 A | 5/1995 | Poulsen et al. |

(Continued)

FOREIGN PATENT DOCUMENTS

| | | |
|---|---|---|
| DE | 195 35 114 A1 | 3/1996 |
| DE | 196 08 027 A1 | 9/1996 |

(Continued)

OTHER PUBLICATIONS

Alfano, R.R., et al., "Fluorescence Spectra From Cancerous and Normal Human Breast and Lung Tissues," *IEEE Journal of Quantum Electronics*. QE–23(10):1806–1811, 1987.

(Continued)

*Primary Examiner*—John P. Leubecker
*Assistant Examiner*—Aaron Roane
(74) *Attorney, Agent, or Firm*—Christensen O'Connor Johnson Kindness PLLC

(57) ABSTRACT

A fluorescence endoscopy video system includes a multi-mode light source that produces light for white light and fluorescence imaging modes. Light from the light source is transmitted through an endoscope to the tissue under observation. The system also includes a compact camera for white light and fluorescence imaging, which may be located in the insertion portion of the endoscope, or attached to the portion of the endoscope outside the body. The camera can be utilized for both white light imaging and fluorescence imaging, and in its most compact form, contains no moving parts.

26 Claims, 9 Drawing Sheets

U.S. PATENT DOCUMENTS

| | | | |
|---|---|---|---|
| 5,421,337 A | 6/1995 | Richards-Kortum et al. | |
| 5,424,841 A | 6/1995 | Van Gelder et al. | |
| 5,430,476 A | 7/1995 | Häfele et al. | |
| 5,485,203 A | 1/1996 | Nakamura et al. | |
| 5,507,287 A | 4/1996 | Palcic et al. | |
| 5,585,846 A | 12/1996 | Kim | |
| 5,590,660 A | 1/1997 | MacAulay et al. | |
| 5,596,654 A | 1/1997 | Tanaka | |
| 5,646,680 A | 7/1997 | Yajima | |
| 5,647,368 A | 7/1997 | Zeng et al. | |
| 5,749,830 A | 5/1998 | Kaneko et al. | |
| 5,772,580 A | 6/1998 | Utsui et al. | |
| 5,827,190 A | 10/1998 | Palcic et al. | |
| 5,891,016 A | 4/1999 | Utsui et al. | |
| 5,986,271 A | 11/1999 | Lazarev et al. | |
| 6,002,137 A | 12/1999 | Hayashi | |
| 6,008,889 A | 12/1999 | Zeng et al. | |
| 6,021,344 A | 2/2000 | Lui et al. | |
| 6,028,622 A * | 2/2000 | Suzuki | 348/65 |
| 6,059,720 A | 5/2000 | Furusawa et al. | |
| 6,069,689 A | 5/2000 | Zeng et al. | |
| 6,070,096 A * | 5/2000 | Hayashi | 600/477 |
| 6,099,466 A | 8/2000 | Sano et al. | |
| 6,120,435 A | 9/2000 | Eino | |
| 6,148,227 A | 11/2000 | Wagnières et al. | |
| 6,161,035 A | 12/2000 | Furusawa | |
| 6,192,267 B1 | 2/2001 | Scherninski et al. | |
| 6,212,425 B1 | 4/2001 | Irion et al. | |
| 6,280,378 B1 | 8/2001 | Kazuhiro et al. | |
| 6,293,911 B1 | 9/2001 | Imaizumi et al. | |
| 6,364,829 B1 | 4/2002 | Fulghum | |
| 6,422,994 B1 | 7/2002 | Kaneko et al. | |
| 6,603,552 B1 | 8/2003 | Cline et al. | |

FOREIGN PATENT DOCUMENTS

| | | |
|---|---|---|
| EP | 2 671 405 | 7/1992 |
| EP | 0 512 965 A1 | 11/1992 |
| EP | 0 774 685 A2 | 5/1997 |
| EP | 0 792 618 A1 | 9/1997 |
| JP | 60-246733 A | 12/1985 |
| JP | 61-159936 A | 7/1986 |
| JP | 07-155285 | 6/1995 |
| JP | 07-155286 | 6/1995 |
| JP | 07-155290 | 6/1995 |
| JP | 07-155291 | 6/1995 |
| JP | 07-155292 | 6/1995 |
| JP | 07-204156 A | 8/1995 |
| JP | 07-222712 | 8/1995 |
| JP | 07-250804 | 10/1995 |
| JP | 07-250812 | 10/1995 |
| JP | 08-224208 A | 9/1996 |
| JP | 08-224209 | 9/1996 |
| JP | 08-224210 A | 9/1996 |
| JP | 08-224240 | 9/1996 |
| JP | 10-127563 | 5/1998 |
| JP | 10-151104 A | 6/1998 |
| JP | 10-201700 A | 8/1998 |
| JP | 10-225426 | 8/1998 |
| JP | 10-243915 | 9/1998 |
| JP | 10-243920 | 9/1998 |
| JP | 10-308114 | 11/1998 |
| JP | 10-309281 | 11/1998 |
| JP | 10-309282 | 11/1998 |
| JP | 10-328129 | 12/1998 |
| JP | 11-089789 | 4/1999 |
| JP | 11-104059 | 4/1999 |
| JP | 11-104060 | 4/1999 |
| JP | 11-104061 | 4/1999 |
| JP | 11-104070 A | 4/1999 |
| JP | 11-113839 | 4/1999 |
| JP | 11-155812 | 6/1999 |
| JP | 08-252218 | 10/1999 |
| JP | 11-332819 | 12/1999 |
| WO | WO 95/26673 | 10/1995 |
| WO | WO 98/24360 | 6/1998 |
| WO | WO 99/01749 A1 | 1/1999 |
| WO | WO 99/53832 A1 | 10/1999 |
| WO | WO 00/42910 | 7/2000 |

OTHER PUBLICATIONS

Andersson–Engles, S. et al., "Tissue Diagnostics Using Laser Induced Fluorescence," *Ber. Bunsenges Physical Chemistry* (93):335–342, 1989.

Hung, J., et al., "Autofluorescence of Normal and Malignant Bronchial Tissue," *Lasers in Surgery and Medicine* (11):99–105, 1991.

* cited by examiner

FILTER 79A

FILTER 79B

FILTER 79C

FILTER 118

FILTER 118

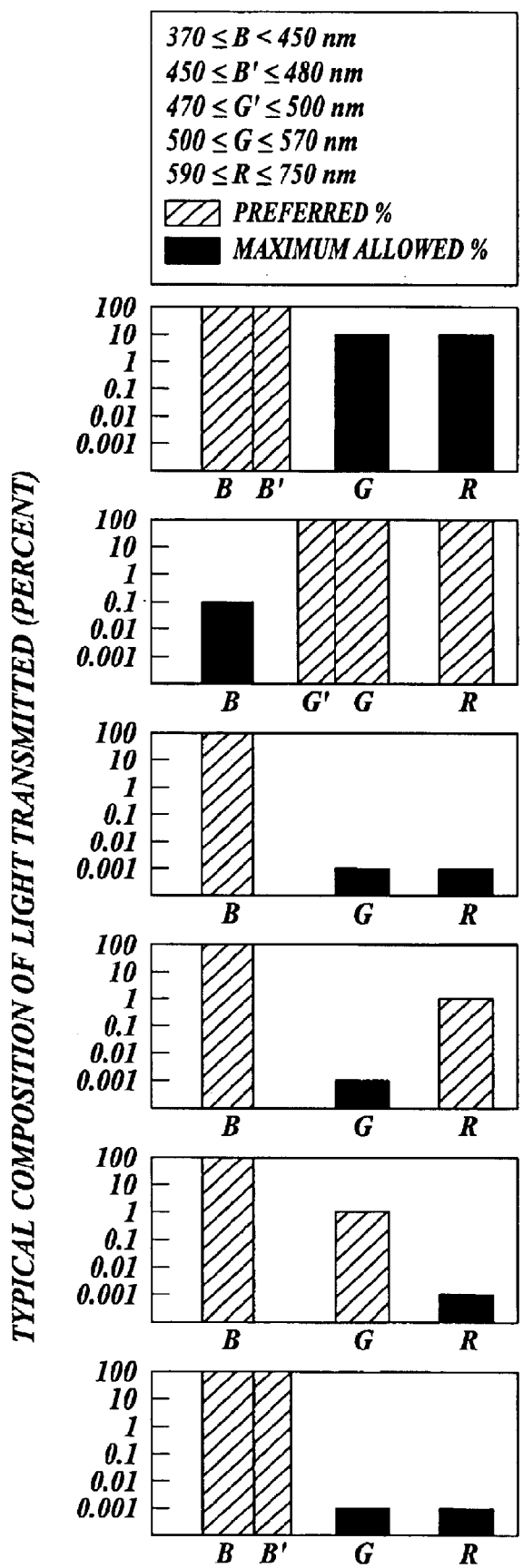

FLUORESCENCE ENDOSCOPY VIDEO SYSTEMS WITH NO MOVING PARTS IN THE CAMERA

FIELD OF THE INVENTION

The present invention relates to medical imaging systems in general, and in particular to fluorescence endoscopy video systems.

BACKGROUND OF THE INVENTION

Fluorescence endoscopy utilizes differences in the fluorescence response of normal tissue and tissue suspicious for early cancer as a tool in the detection and localization of such cancer. The fluorescing compounds or fluorophores that are excited during fluorescence endoscopy may be exogenously applied photo-active drugs that accumulate preferentially in suspicious tissues, or they may be the endogenous fluorophores that are present in all tissue. In the latter case, the fluorescence from the tissue is typically referred to as autofluorescence or native fluorescence. Tissue autofluorescence is typically due to fluorophores with absorption bands in the UV and blue portion of the visible spectrum and emission bands in the green to red portions of the visible spectrum. In tissue suspicious for early cancer, the green portion of the autofluorescence spectrum is significantly suppressed. Fluorescence endoscopy that is based on tissue autofluorescence utilizes this spectral difference to distinguish normal from suspicious tissue.

Since the concentration and/or quantum efficiency of the endogenous fluorophores in tissue is relatively low, the fluorescence emitted by these fluorophores is not typically visible to the naked eye. Fluorescence endoscopy is consequently performed by employing low light image sensors to acquire images of the fluorescing tissue through the endoscope. The images acquired by these sensors are most often encoded as video signals and displayed on a color video monitor. Representative fluorescence endoscopy video systems that image tissue autofluorescence are disclosed in U.S. Pat. No. 5,507,287, issued to Palcic et al.; U.S. Pat. No. 5,590,660, issued to MacAulay et al.; U.S. Pat. No. 5,827,190, issued to Palcic et al., U.S. patent application Ser. Nos. 09/615,965, and 09/905,642, all of which are herein incorporated by reference. Each of these is assigned to Xillix Technologies Corp. of Richmond, British Columbia, Canada, the assignee of the present application.

While the systems disclosed in the above-referenced patents are significant advances in the field of early cancer detection, improvements can be made. In particular, it is desirable to reduce the size, cost, weight, and complexity of the camera described for these systems by eliminating moving parts.

SUMMARY OF THE INVENTION

A fluorescence endoscopy video system in accordance with the present invention includes an endoscopic light source that is capable of operating in multiple modes to produce either white light, reflectance light, fluorescence excitation light, or fluorescence excitation light with reference reflectance light. An endoscope incorporates a light guide for transmitting light to the tissue under observation and includes either an imaging guide or a camera disposed in the insertion portion of the endoscope for receiving light from the tissue under observation. A compact camera with at least one low light imaging sensor that receives light from the tissue and is capable of operating in multiple imaging modes to acquire color or multi-channel fluorescence and reflectance images. The system further includes an image processor and system controller that digitizes, processes and encodes the image signals produced by the image sensor(s) as a color video signal and a color video monitor that displays the processed video images.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 8A–8F are graphs illustrating presently preferred transmission characteristics of filters for color imaging, fluorescence/fluorescence imaging, and fluorescence/reflectance imaging with the camera embodiment shown in FIGS. 7A–7B.

DETAILED DESCRIPTION OF THE PREFERRED EMBODIMENT

Figure 1A:
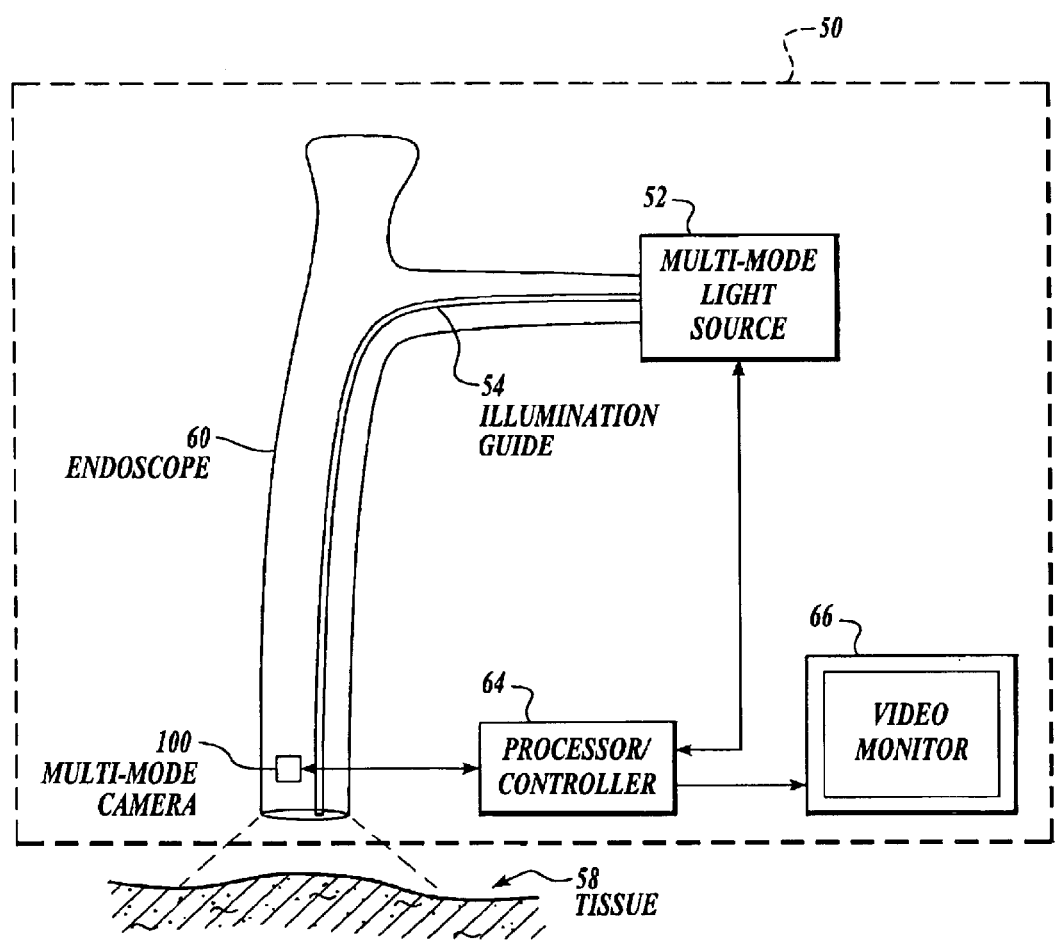
FIGS. 1A–1B are block diagrams of a fluorescence endoscopy video system according to one embodiment of the present invention.

FIG. 1A is a block diagram of a fluorescence endoscopy video system 50 in accordance with one embodiment of the present invention. The system includes a multi-mode light source 52 that generates light for obtaining color and fluorescence images. The use of the light source for obtaining different kinds of images will be described in further detail below. Light from the light source 52 is supplied to an illumination guide 54 of an endoscope 60, which then illuminates a tissue sample 58 that is to be imaged.

As shown in FIG. 1A, the system also includes a multi-mode camera 100, which is located at the insertion end of the endoscope 60. The light from the tissue is directly captured by the multi-mode camera 100. With the multi-mode camera 100 located at the insertion end of the endoscope, the resulting endoscope 60 can be characterized as a fluorescence video endoscope, similar to video endoscopes currently on the market (such as the Olympus CF-240L) in utility, but with the ability to be utilized for fluorescence/ reflectance and/or fluorescence/fluorescence imaging, in additional to conventional color imaging. Fluorescence/reflectance and fluorescence/fluorescence imaging will be described in detail below. By locating the camera at the insertion end of the endoscope, the inherent advantages of a video endoscope can be obtained: namely, the light available to form an image and the image resolution are improved compared to the case when the image is transmitted outside the body through an endoscope imaging guide or relay lens system.

A processor/controller 64 controls the multi-mode camera 100 and the light source 52, and produces video signals that are displayed on a video monitor 66. The processor/controller 64 communicates with the multi-mode camera 100 with wires or other signal carrying devices that are routed within the endoscope. Alternatively, communication between the processor/controller 64 and the camera 100 can be conducted over a wireless link.

Figure 1B:
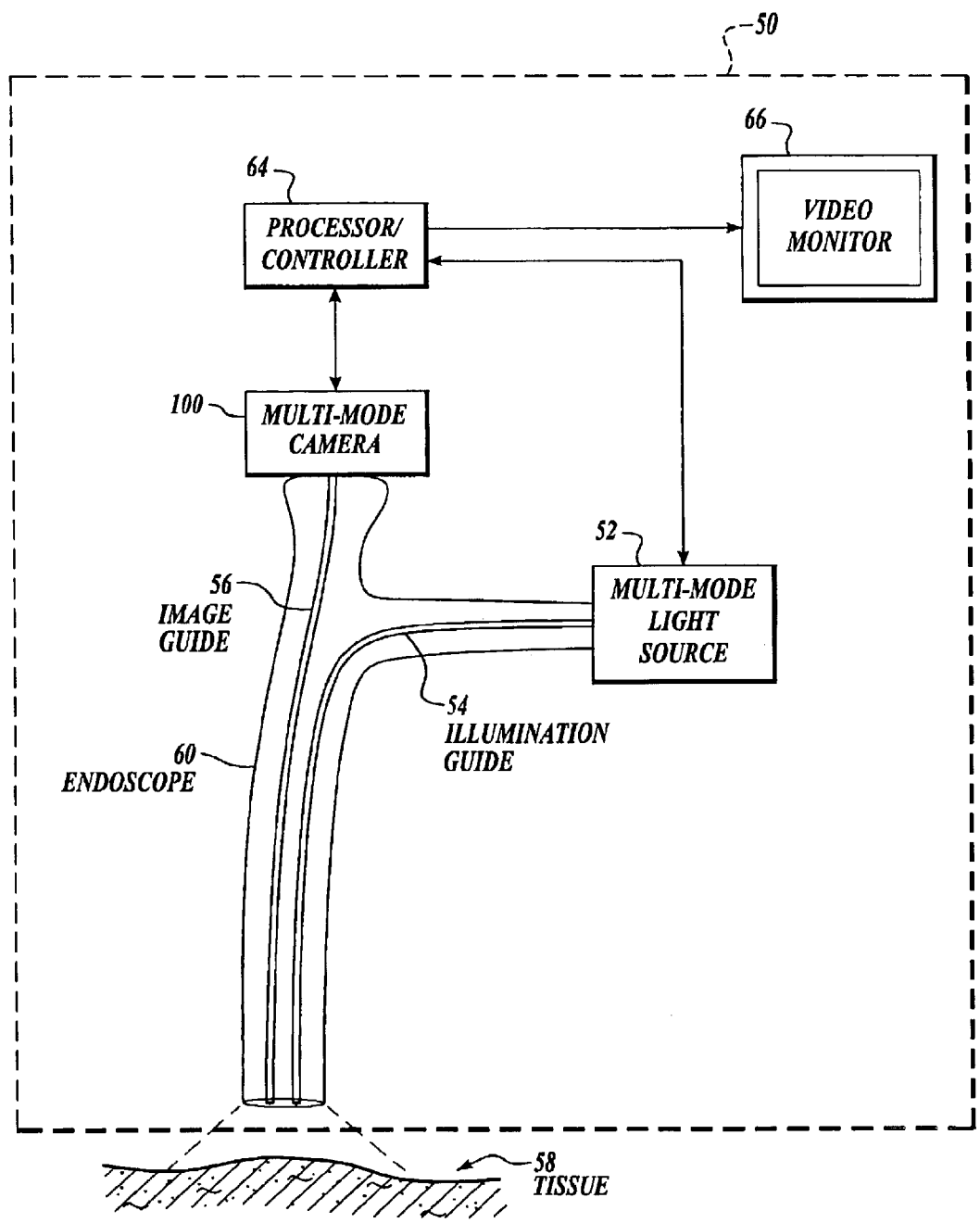

FIG. 1B is a block diagram of an alternative fluorescence endoscopy video system 50, which differs from that shown in FIG. 1A in that endoscope 60 also incorporates an image guide 56 and the multi-mode camera 100 is attached to an external portion of the endoscope that is outside the body. The light that is collected from the tissue by endoscope 60 is transmitted through the image guide 56 and projected into the multi-mode camera 100. Other than the addition of the image guide 56 to endoscope 100 and the location of the multi-mode camera 100 at the external end of the endoscope, the system of FIG. 1B is identical to that shown in FIG. 1A.

Figure 2A:
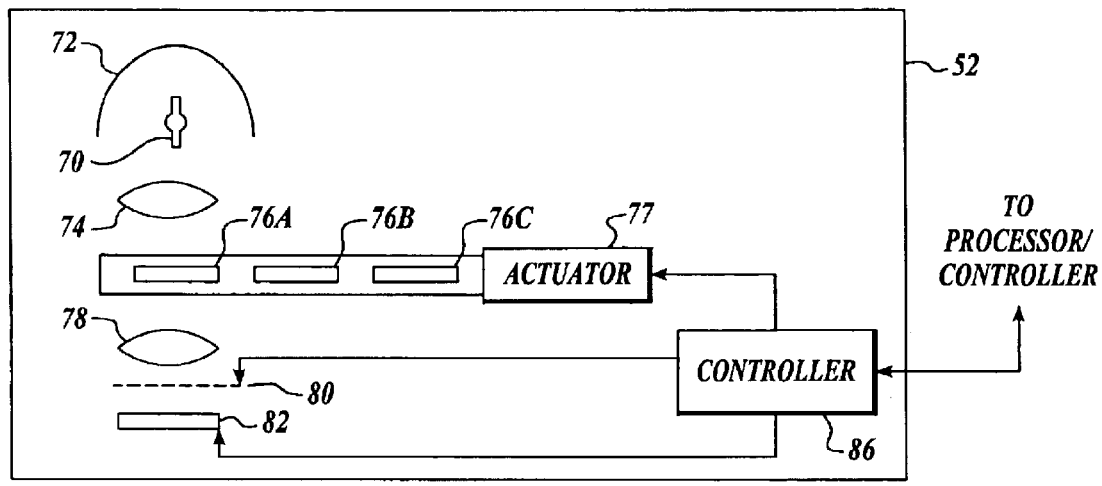
FIGS. 2A–2B are block diagrams of a multi-mode light source in accordance with different embodiments of the present invention.
Figure 2A:
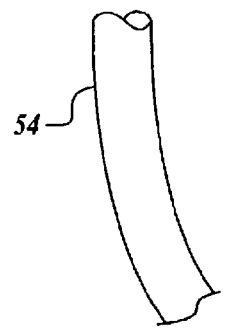

FIG. 2A shows the components of the light source 52 in greater detail. The light source 52 includes an arc lamp 70 that is surrounded by a reflector 72. In the preferred embodiment of the invention, the arc lamp 70 is a high pressure mercury arc lamp (such as the Osram VIP R 150/P24). Alternatively, other arc lamps, solid state devices (such as light emitting diodes or diode lasers), or broadband light sources may be used, but a high pressure mercury lamp is currently preferred for its combination of high blue light output, reasonably flat white light spectrum, and small arc size.

The light from the arc lamp 70 is coupled to a light guide 54 of the endoscope 60 through appropriate optics 74, 76, and 78 for light collection, spectral filtering and focusing respectively. The light from the arc lamp is spectrally filtered by one of a number of optical filters 76A, 76B, 76C . . . that operate to pass or reject desired wavelengths of light in accordance with the operating mode of the system. As used herein, "wavelength" is to be interpreted broadly to include not only a single wavelength, but a range of wavelengths as well.

An intensity control 80 that adjusts the amount of light transmitted along the light path is positioned at an appropriate location between the arc lamp 70 and the endoscope light guide 54. The intensity control 80 adjusts the amount of light that is coupled to the light guide 54. In addition, a shutter mechanism 82 may be positioned in the same optical path in order to block any of the light from the lamp from reaching the light guide. A controller 86 operates an actuator 77 that moves the filters 76A, 76B or 76C into and out of the light path. The controller 86 also controls the position of the intensity control 80 and the operation of the shutter mechanism 82.

The transmission characteristics of filters 76A, 76B, 76C, . . . , the characteristics of the actuator 77 mechanism, and the time available for motion of the filters 76A, 76B, 76C, . . . , into and out of the light path, depend on the mode of operation required for use with the various camera embodiments. The requirements fall into two classes. If the light source shown in FIG. 2A is of the class wherein only one filter is utilized per imaging mode, the appropriate filter is moved in or out of the light path only when the imaging mode is changed. In that case, the actuator 77 only need change the filter in a time of approximately 1.0 second. The optical filter characteristics of filters 76A, 76B . . . are tailored for each imaging mode. For example, optical filter 76A, used for color imaging, reduces any spectral peaks and modifies the color temperature of the arc lamp 70 so that the output spectrum simulates sunlight. Optical filter 76B transmits only fluorescence excitation light for use with the fluorescence/fluorescence imaging mode and optical filter 76C transmits both fluorescence excitation light and reference reflectance light for use with the fluorescence/reflectance imaging mode.

Figure 2B:
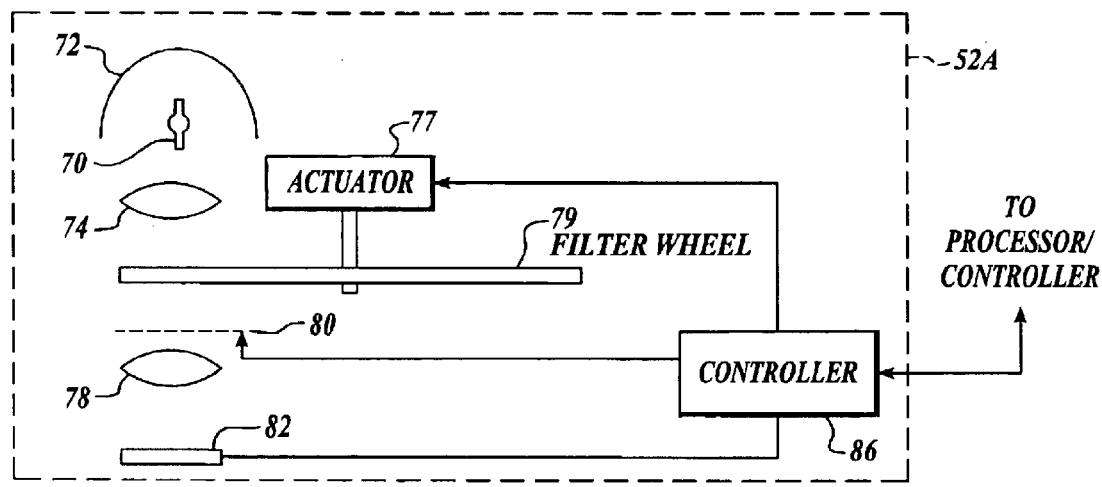
Figure 2B:
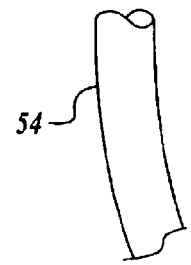
Figure 3:
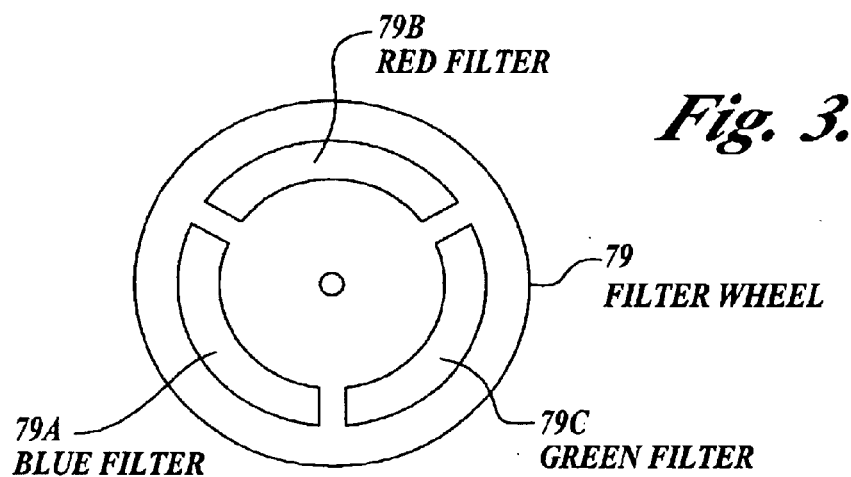
FIG. 3 shows a filter wheel and optical filters for the multi-mode light source.

A light source 52A of a second class is illustrated in FIG. 2B; only the differences from the light source shown in FIG. 2A will be elucidated. The light source 52A uses multiple filters during each imaging mode. For example, light source filters, which provide red, green, and blue illumination sequentially for periods corresponding to a video frame or field, can be used for the acquisition of a color or a multi-spectral image with a monochrome image sensor, with the different wavelength components of the image each acquired at slightly different times. Such rapid filter changing requires a considerably different actuator than necessitated for the light source 52 of FIG. 2A. As shown in FIG. 2B, the filters are mounted on a filter wheel 79 that is rotated by a motor, which is synchronized to the video field or frame rate. The layout of the blue, red and green filters, 79A, 79B, and 79C respectively, in filter wheel 79 are shown in FIG. 3.

The transmission characteristics of light source filters, the characteristics of the filter actuator mechanism, and the time available for motion of the filters into and out of the light path, for the two different classes of light sources are described in more detail below in the context of the various camera embodiments.

Because fluorescence endoscopy is generally used in conjunction with white light endoscopy, each of the various embodiments of the multi-mode camera 100 described below may be used both for color and fluorescence/reflectance and/or fluorescence/fluorescence imaging. These camera embodiments particularly lend themselves to incorporation within a fluorescence video endoscope due to their compactness and their ability to be implemented with no moving parts.

Figure 4A:
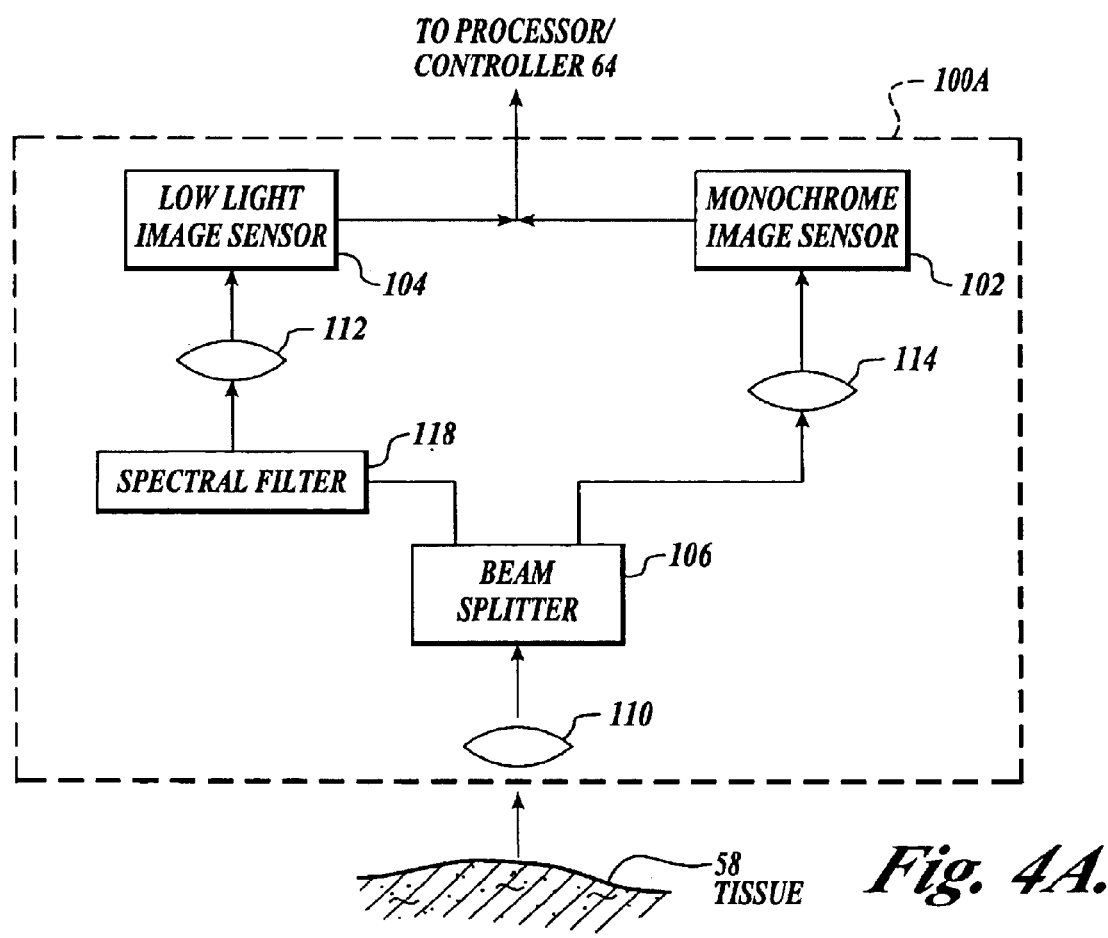
FIGS. 4A–4C illustrate a number of alternative embodiments of a camera that can acquire color and/or fluorescence/reflectance images according to one embodiment of the present invention with optional placement for collimation and imaging optics.
Figure 5A:
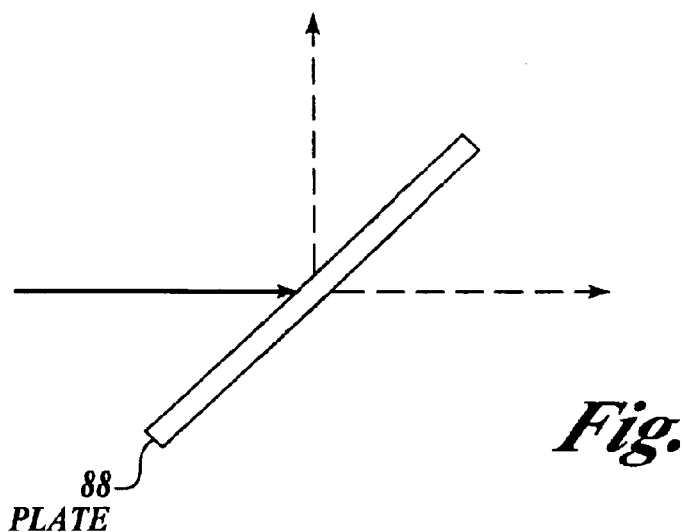
FIGS. 5A–5C illustrate a number of camera beamsplitter configurations.
Figure 5B:
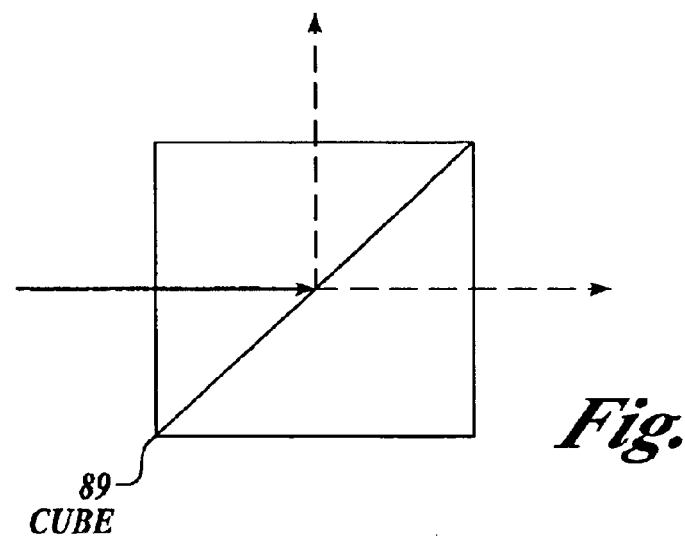
Figure 5C:
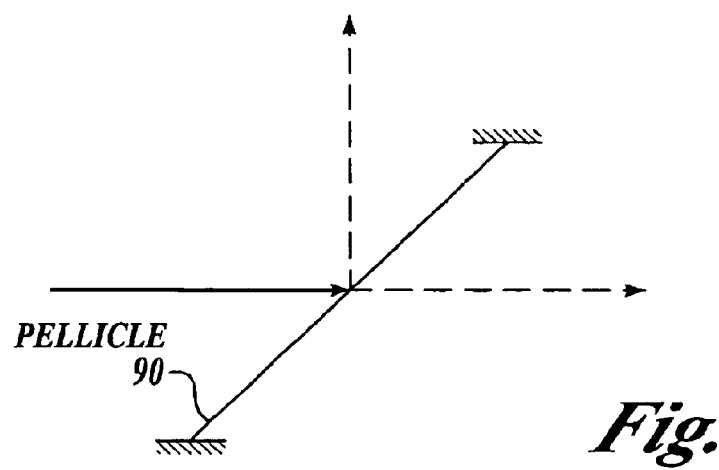

In a first embodiment, shown in FIG. 4A, a camera 100A receives light from the tissue 58, either directly from the tissue in the case of a camera located at the insertion end of an endoscope, as shown in FIG. 1A, or by virtue of an endoscope image guide 56, which transmits the light from the tissue to the camera, as shown in FIG. 1B. The light is directed towards a monochrome image sensor 102 and a low light image sensor 104 by a fixed optical beamsplitter 106 that splits the incoming light into two beams. The light beam is split such that a smaller proportion of the light received from the tissue 58 is directed towards the monochrome image sensor 102 and a larger proportion of the incoming light is directed towards the low light image sensor 104. In this embodiment, the beamsplitter may be a standard commercially available single plate 88, single cube 89, or single pellicle design 90, as shown in FIGS. 5A–5C. It should be noted that, if the optical path between the tissue 58 and the image sensors contains an uneven number of reflections (e.g., such as from a single component beamsplitter), the image projected onto the sensor will be left-to-right inverted. The orientation of such images will need to be corrected by image processing.

In FIG. 4A, light collimating optics 110 are positioned in front of the beamsplitter 106, and imaging optics 112 and 114 are positioned immediately preceding the monochrome image sensor 102 and the low light image sensor 104, respectively. A spectral filter 118 is located in the optical path between the beamsplitter 106 and the low light image sensor 104. Alternatively, the spectral filter 118 may be incorporated as an element of the beamsplitter 106.

Figure 4B:
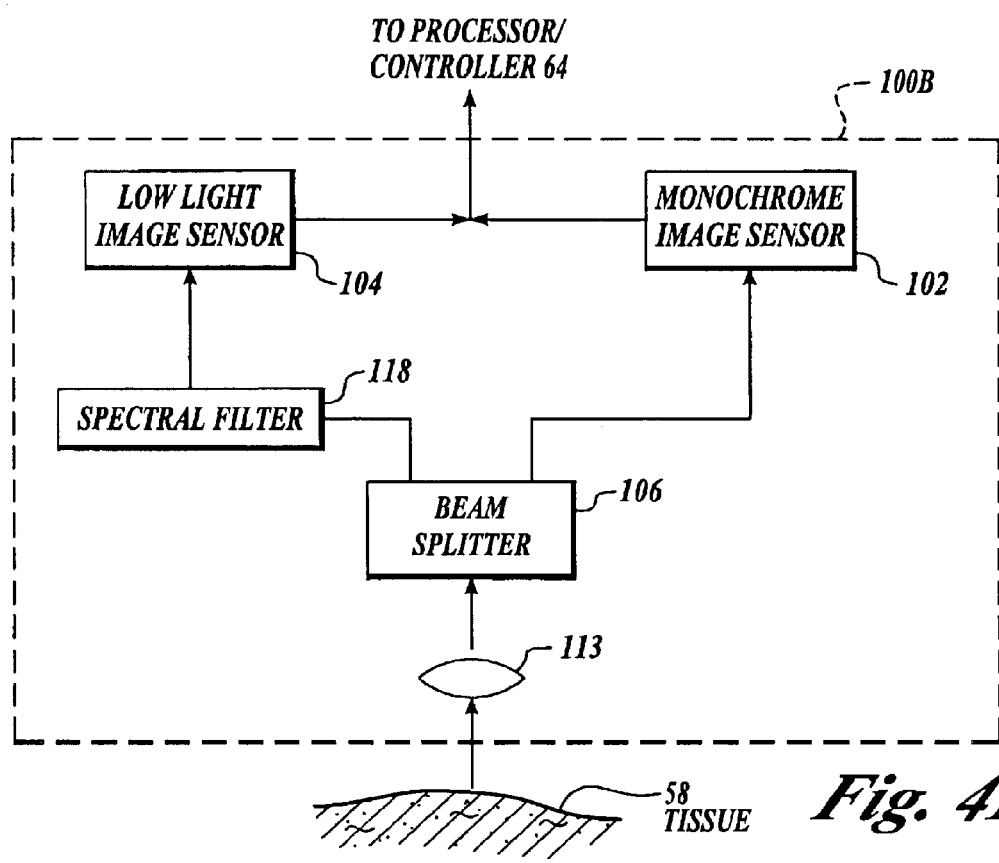

FIG. 4B illustrates another embodiment of the camera 100. A camera 100B is the same as the camera 100A described above except that the light collimating optics 110 and imaging optics 112 and 114 have been eliminated and replaced with a single set of imaging optics 113 located between the tissue and beamsplitter 106. The advantage of this configuration is that all imaging is performed and controlled by the same imaging optics 113. Such a configuration requires all beam paths to have the same optical path length, however, and this restriction must be considered in the design of the beamsplitter 106 and spectral filter 118 that is located in the path to the low light image sensor 104. In addition, the fact that these optical elements are located in a converging beam path must be considered in specifying these elements and in the design of the imaging optics 113.

The low light image sensor 104 preferably comprises a charge coupled device with charge carrier multiplication (of the same type as the Texas Instruments TC253 or the Marconi Technologies CCD65), electron beam charge coupled device (EBCCD), intensified charge coupled device (ICCD), charge injection device (CID), charge modulation device (CMD), complementary metal oxide semiconductor image sensor (CMOS) or charge coupled device (CCD) type sensor. The monochrome image sensor 102 is preferably a CCD or a CMOS image sensor.

Figure 4C:
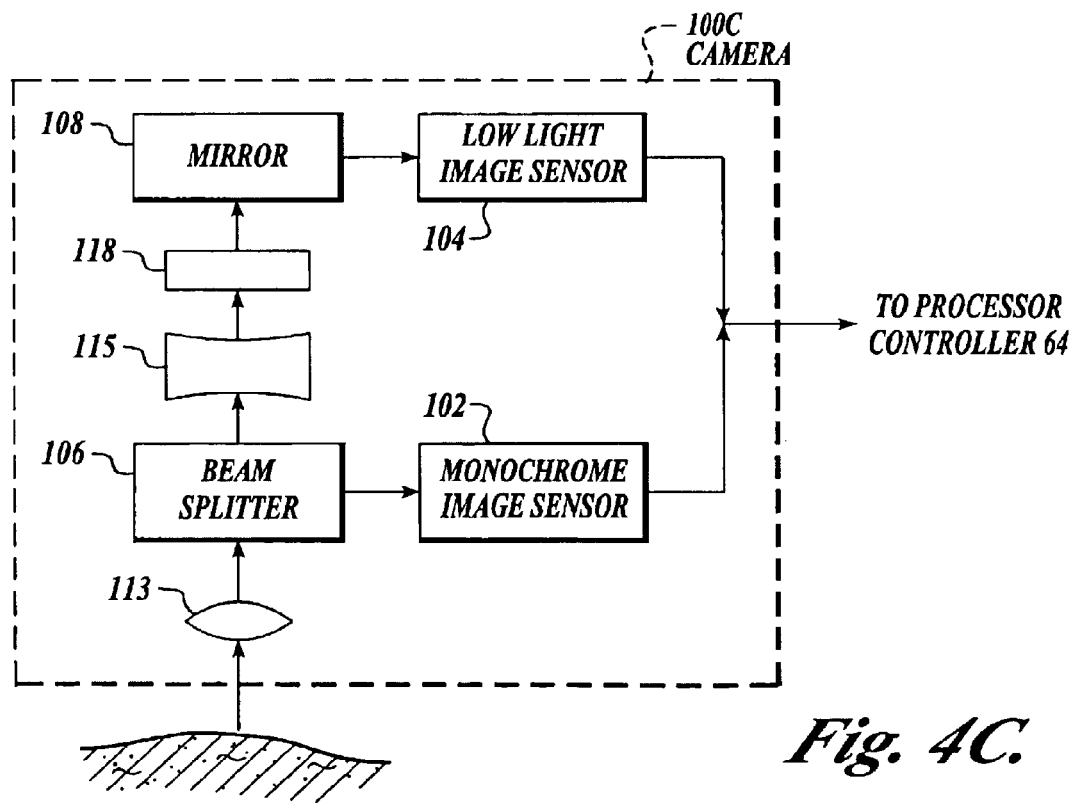

An alternative configuration of the camera 100B is shown in FIG. 4C. All aspects of this embodiment of this camera 110C are similar to the camera 100B shown in FIG. 4B except for differences which arise from reducing the width of the camera by mounting both image sensors 102 and 104 perpendicular to the camera front surface. In this alternative configuration, the low light image sensor 104 and the monochrome image sensor 102 are mounted with their image planes perpendicular to the input image plane of the camera. Light received from the tissue 58 is projected by imaging optics 113 through beamsplitter 106 onto the image sensors 102 and 104. The beamsplitter 106 directs a portion of the incoming light in one beam towards one of the sensors 102, 104. Another portion of the incoming light in a second light beam passes straight through the beamsplitter 106 and is directed by a mirror 108 towards the other of the sensors 102, 104. In addition, a second set of imaging optics 115 is utilized to account for the longer optical path to this second sensor. The images projected onto both sensors will be left-to-right inverted and should be inverted by image processing.

The processor/controller 64 as shown in FIGS. 1A and 1B receives the transduced image signals from the camera 100 and digitizes and processes these signals. The processed signals are then encoded in a video format and displayed on a color video monitor 66.

Based on operator input, the processor/controller 64 also provides control functions for the fluorescence endoscopy video system. These control functions include providing control signals that control the camera gain in all imaging modes, coordinating the imaging modes of the camera and light source, and providing a light level control signal for the light source.

The reason that two separate images in different wavelength bands are acquired in fluorescence imaging modes of the fluorescence endoscopy video systems described herein, and the nature of the fluorescence/reflectance and fluorescence/fluorescence imaging, will now be explained. It is known that the intensity of the autofluorescence at certain wavelengths changes as tissues become increasingly abnormal (i.e. as they progress from normal to frank cancer). When visualizing images formed from such a band of wavelengths of autofluorescence, however, it is not easy to distinguish between those changes in the signal strength that are due to pathology and those that are due to imaging geometry and shadows. A second fluorescence image acquired in a band of wavelengths in which the image signal is not significantly affected by tissue pathology, utilized for fluorescence/fluorescence imaging, or a reflected light image acquired in a band of wavelengths in which the image signal is not significantly affected by tissue pathology consisting of light that has undergone scattering within the tissue (known as diffuse reflectance), utilized for fluorescence/reflectance imaging, may be used as a reference signal with which the signal strength of the first fluorescence image can be "normalized". Such normalization is described in two patents previously incorporated herein by reference: U.S. Pat. No. 5,507,287, issued to Palcic et al. describes fluorescence/fluorescence imaging and U.S. Pat. No. 5,590,660, issued to MacAulay et al. describes fluorescence/reflectance imaging.

One technique for performing the normalization is to assign each of the two image signals a different display color, e.g., by supplying the image signals to different color inputs of a color video monitor. When displayed on a color video monitor, the two images are effectively combined to form a single image, the combined color of which represents the relative strengths of the signals from the two images. Since light originating from fluorescence within tissue and diffuse reflectance light which has undergone scattering within the tissue are both emitted from the tissue with a similar spatial distribution of intensities, the color of a combined image is independent of the absolute strength of the separate image signals, and will not change as a result of changes in the distance or angle of the endoscope 60 to the tissue sample 58, or changes in other imaging geometry factors. If, however, there is a change in the shape of the autofluorescence spectrum of the observed tissue that gives rise to a change in the relative strength of the two image signals, such a change will be represented as a change in the color of the displayed image. Another technique for performing the normalization is to calculate the ratio of the pixel intensities at each location in the two images. A new image can then be created wherein each pixel has an intensity and color related to the ratio computed. The new image can then be displayed by supplying it to a color video monitor.

The mixture of colors with which normal tissue and tissue suspicious for early cancer are displayed depends on the gain applied to each of the two separate image signals. There is an optimal gain ratio for which tissue suspicious for early cancer in a fluorescence image will appear as a distinctly different color than normal tissue. This gain ratio is said to provide the operator with the best combination of sensitivity (ability to detect suspect tissue) and specificity (ability to discriminate correctly). If the gain applied to the reference image signal is too high compared to the gain applied to the fluorescence image signal, the number of tissue areas that appear suspicious, but whose pathology turns out to be normal, increases. Conversely, if the relative gain applied to the reference image signal is too low, sensitivity decreases and suspect tissue will appear like normal tissue. For optimal system performance, therefore, the ratio of the gains applied to the image signals must be maintained at all times. The control of the gain ratio is described in two patent applications previously incorporated herein by reference: U.S. patent application Ser. Nos. 09/615,965, and 09/905,642.

In vivo spectroscopy has been used to determine which differences in tissue autofluorescence and reflectance spectra have a pathological basis. The properties of these spectra determine the particular wavelength bands of autofluorescence and reflected light required for the fluorescence/reflectance imaging mode, or the particular two wavelength bands of autofluorescence required for fluorescence/fluorescence imaging mode. Since the properties of the spectra depend on the tissue type, the wavelengths of the important autofluorescence band(s) may depend on the type of tissue being imaged. The specifications of the optical filters described below are a consequence of these spectral characteristics, and are chosen to be optimal for the tissues to be imaged.

As indicated above, the filters in the light source and camera should be optimized for the imaging mode of the camera, the type of tissue to be examined and/or the type of pre-cancerous tissue to be detected. Although all of the filters described below can be made to order using standard, commercially available components, the appropriate wavelength range of transmission and degree of blocking outside of the desired transmission range for the described fluorescence endoscopy images are important to the proper operation of the system. The importance of other issues in the specification of such filters, such as the fluorescence properties of the filter materials and the proper use of anti-reflection coatings, are taken to be understood.

FIGS. 6A–6E illustrate the preferred filter characteristics for use in a fluorescence endoscopy system having a camera of the type shown in FIGS. 4A–4C and light source as shown in FIG. 2B, that operates in a fluorescence/reflectance imaging mode, or a color imaging mode. There are several possible configurations of fluorescence endoscopy video systems, operating in the fluorescence/reflectance imaging mode including green fluorescence with either red or blue reflectance, and red fluorescence with either green or blue reflectance. The particular configuration utilized depends on the target clinical organ and application. The filter characteristics will now be described for each of these four configurations.

Figure 6A:
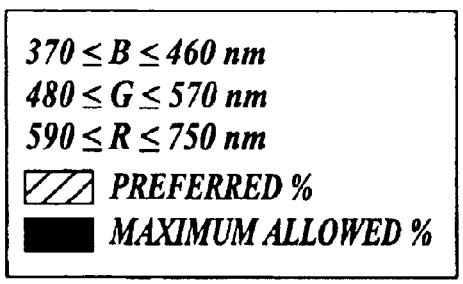
FIGS. 6A–6E are graphs illustrating presently preferred transmission characteristics of filters utilized for color imaging and fluorescence/reflectance imaging with the camera embodiments shown in FIGS. 4A–4C.
Figure 6A:
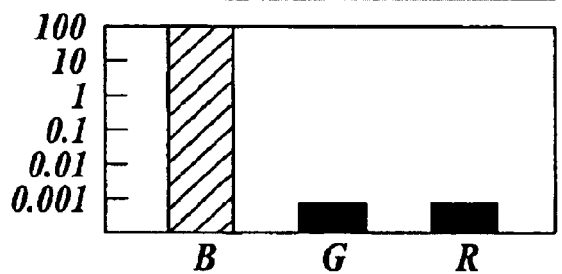

FIG. 6A illustrates the composition of the light transmitted by a blue filter, such as filter 79A, which is used to produce excitation light in the system light source. This filter transmits light in the wavelength range from 370–460 nm or any subset of wavelengths in this range. Of the light transmitted by this filter, less than 0.001% is in the fluorescence imaging band from 480–750 nm (or whatever desired subsets of this range is within the specified transmission range of the primary and reference fluorescence image filters described below).

Figure 6B:
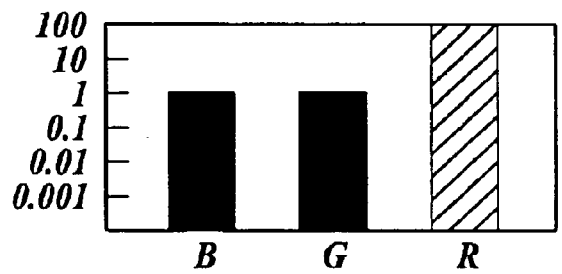

FIG. 6B illustrates the composition of the light transmitted by a red filter, such as filter 79B, which is used to produce red reflectance light in the system light source. This filter transmits light in the wavelength range from 590–750 nm or any subset of wavelengths in this range. Light transmitted outside this range should not exceed 1%.

Figure 6C:
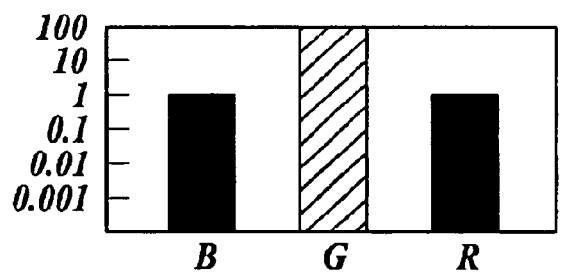

FIG. 6C illustrates the composition of the light transmitted by a green filter, such as filter 79C, which is used to produce green reflectance light in the system light source. This filter transmits light in the wavelength range from 480–570 nm or any subset of wavelengths in this range. Light transmitted outside this range should not exceed 1%.

Figure 6D:
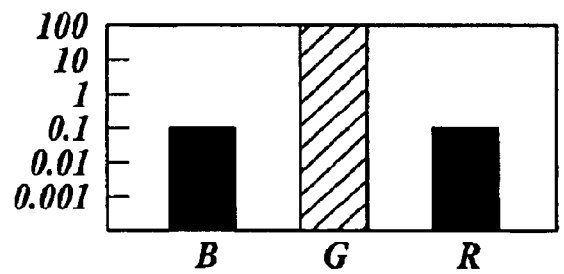

FIG. 6D shows the composition of the light transmitted by a camera spectral filter, such as filter 118, for defining the primary fluorescence image in the green spectral band. In this configuration, the filter blocks excitation light and red fluorescence light while transmitting green fluorescence light in the wavelength range of 480–570 nm or any subset of wavelengths in this range. When used in a fluorescence endoscopy video system with the light source filter 79A described above, the filter characteristics are such that any light outside of the wavelength range of 480–570 nm, or any desired subset of wavelengths in this range, contributes no more than 0.1% to the light transmitted by the filter.

Figure 6E:
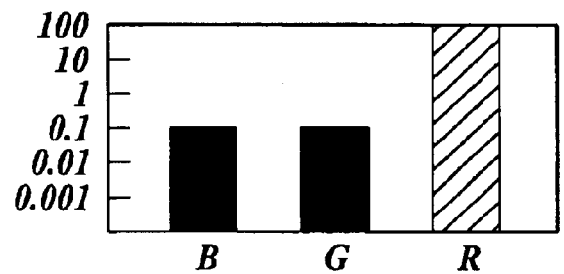

FIG. 6E shows the composition of the light transmitted by a camera filter, such as filter 118, for defining the primary fluorescence image in the red spectral band. In this configuration, the filter blocks excitation light and green fluorescence light while transmitting red fluorescence light in the wavelength range of 590–750 nm or any subset of wavelengths in this range. When used in a fluorescence endoscopy video system with the light source filter 79A described above, the filter characteristics are such that any light outside of the wavelength range of 590–750 nm, or any desired subset of wavelengths in this range, contributes no more than 0.1% to the light transmitted by the filter.

The operation of the preferred embodiment of the fluorescence endoscopy video system will now be described. The cameras 100A as shown in FIG. 4A and 100B as shown in FIG. 4B or 100C as shown in FIG. 4C are capable of operating in color and fluorescence/reflectance imaging modes. A light source of the type shown in FIG. 2B, that provides a different output every video frame or field is required. In the color imaging mode, the processor/controller 64 provides a control signal to the multi-mode light source 52 that indicates the light source should be operating in the white light mode and provides a synchronizing signal. The light source 52 sequentially outputs filtered red, green, and blue light, synchronously with the video field or frame of the image sensors 102 and 104. The filtered light from the light source 52 is projected into the endoscope light guide 54 and is transmitted to the tip of the endoscope 60 to illuminate the tissue 58.

The processor/controller 64 also protects the sensitive low light image sensor 104 during color imaging by decreasing the gain of the amplification stage of the sensor. The light reflected by the tissue 58 is collected and transmitted by the endoscope image guide 56 to the camera where it is projected through beamsplitter 106 onto the monochrome image sensor 102, or the light is directly projected through the camera beamsplitter 106 onto the monochrome image sensor 102 if the sensor is located within the insertion portion of the endoscope. The image projected during each of red, green, and blue illuminations is transduced by the monochrome image sensor 102 and the resulting image signals are transmitted to the processor/controller 64.

Based on the brightness of the images captured, the processor/controller 64 provides a control signal to the multi-mode light source 52 to adjust the intensity control 80 and thereby adjust the level of light output by the endoscope light guide 54. The processor/controller 64 may also send a control signal to the camera 100A, 100B or 100C to adjust the gain of the monochrome image sensor 102.

The processor/controller 64 interpolates the images acquired during sequential periods of red, green, and blue illumination to create a complete color image during all time periods, and encodes that color image as video signals. The video signals are connected to color video monitor 66 for display of the color image. All of the imaging operations occur at analog video display rates (30 frames per second for NTSC format and 25 frames per second for PAL format).

When switching to the fluorescence/reflectance imaging mode, the processor/controller 64 provides a control signal to the multi-mode light source 52 to indicate that it should be operating in fluorescence/reflectance mode. In response to this signal, the light source filter wheel 79 stops rotating and the light source 52 selects and positions the appropriate blue optical filter 79A continuously into the optical path between the arc lamp 70 and the endoscope light guide 54. This change from sequentially changing filters to a static filter occurs in a period of approximately one second. Filter 79A transmits only those wavelengths of light that will induce the tissue 58 under examination to fluoresce. All other wavelengths of light are substantially blocked as described above. The filtered light is then projected into the endoscope light guide 54 and transmitted to the tip of the endoscope 60 to illuminate the tissue 58.

As part of setting the system in the fluorescence/reflectance mode, the processor/controller 64 also increases the gain of the amplification stage of the low light image sensor 104. The fluorescence emitted and excitation light reflected by the tissue 58 are either collected by the endoscope image guide 56 and projected through the camera beamsplitter 106 onto the low light image sensor 104 and the image sensor 102, or are collected and directly projected through the camera beamsplitter 106 onto the low light image sensor 104 and the image sensor 102 at the insertion tip of the endoscope 60. Spectral filter 118 limits the light transmitted to the low light image sensor 104 to either green or red autofluorescence light only and substantially blocks the light in the excitation wavelength band. The autofluorescence image is transduced by the low light image sensor 104. The reference reflected excitation light image is transduced by the monochrome image sensor 102 and the resulting image signals are transmitted to the processor/controller 64.

Based on the brightness of the transduced images, the processor/controller 64 may provide a control signal to the multi-mode light source 52 to adjust the intensity control 80 and thereby adjust the level of light delivered to the endoscope 60. The processor/controller 64 may also send control signals to the cameras 100A, 100B or 100C to adjust the gains of the low light image sensor 104 and the monochrome image sensor 102, in order to maintain constant image brightness while keeping the relative gain constant.

After being processed, the images from the two sensors are encoded as video signals by processor/controller 64. The fluorescence/reflectance image is displayed by applying the video signals to different color inputs on the color video monitor 66.

In order for the combined image to have optimal clinical meaning, for a given proportion of fluorescence to reference light signals emitted by the tissue and received by the system, a consistent proportion must also exist between the processed image signals that are displayed on the video monitor. This implies that the (light) signal response of the fluorescence endoscopy video system is calibrated. The calibration technique is described in two patent applications previously incorporated herein by reference: U.S. patent application Ser. Nos. 09/615,965, and 09/905,642.

The cameras 100A, 100B, 100C can be operated in a variation of the fluorescence/reflectance mode to simulta- neously obtain fluorescence images and reflectance images with red, green, and blue illumination. The operation of the system is similar to that described previously for color imaging, so only the points of difference from the color imaging mode will be described.

In this variation of the fluorescence/reflectance mode, instead of changing from sequential red, green, and blue illumination to static blue illumination when switching from color imaging to fluorescence/reflectance imaging, the multi-mode light source 52 provides the same sequential illumination utilized in the color imaging mode, for all imaging modes. Capture and display of the light reflected by the tissue is similar to that described previously for the color imaging mode. However, in addition to the reflectance images captured in that mode, the gain of the amplification stage of the low light image sensor 104 is adjusted to a value that makes it possible to capture autofluorescence images during blue illumination. During red and green illumination, the gain of amplification stage of the low light sensor is decreased to protect the sensor while the image sensor 102 captures reflectance images.

In this modified fluorescence/reflectance mode, the camera captures both reflectance and fluorescence images during the blue illumination period, in addition to reflected light images during the red and green illumination periods. As for the color imaging mode, the reflectance images are interpolated and displayed on the corresponding red, green and blue channels of a color video monitor to produce a color image. Like the previously described fluorescence/reflectance mode, a fluorescence/reflectance image is produced by overlaying the fluorescence image and one or more of the reflectance images displayed in different colors on a color video monitor.

Since individual reflectance and fluorescence images are concurrently captured, both a color image and a fluorescence/reflectance image can be displayed simultaneously on the color video monitor. In this case, there is no need to utilize a separate color imaging mode. Alternatively, as described for the previous version of fluorescence/reflectance operation, only the fluorescence/reflectance image may be displayed during fluorescence/reflectance imaging and a color image displayed solely in the color imaging mode.

Yet another embodiment of this invention will now be described. All points of similarity with the first embodiment will be assumed understood and only points that differ will be described.

Figure 7A:
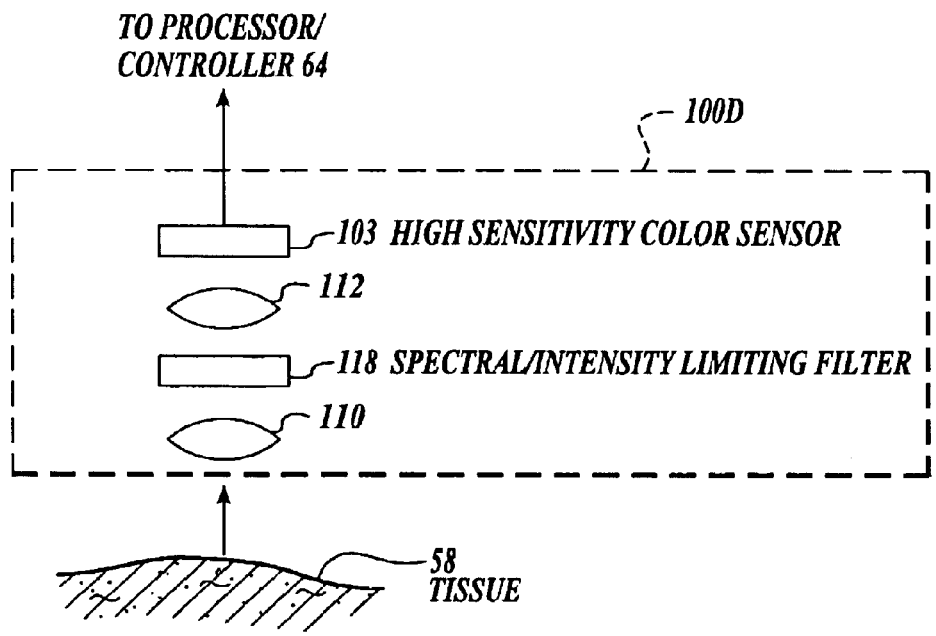
FIGS. 7A–7B illustrate additional embodiments of a camera according to the present invention that can acquire color, fluorescence/reflectance, and/or fluorescence/fluorescence images according to an embodiment of the present invention with optional placement for collimation and imaging optics.

In this second embodiment, all aspects of the fluorescence endoscopy video system are similar to those of the first embodiment except for the camera and the light source. A camera 100D for this embodiment of a system is as shown in FIG. 7A. It differs from the cameras 100A, 100B or 100C as described above in that all imaging modes utilize a single, low light color image sensor 103 (preferably a color CCD with charge carrier multiplication such as the Texas Instruments TC252) and that no beamsplitter is required. Alternatively, the color image sensor 103 may be a three-CCD with charge carrier multiplication color image sensor assembly, a color CCD, a three-CCD color image sensor assembly, a color CMOS image sensor, or a three-CMOS color image sensor assembly.

Each of the pixel elements on the low light color sensor 103 is covered by an integrated filter, typically red, green or blue. These filters define the wavelength bands of fluorescence and reflectance light that reach the individual pixel elements. Such mosaic filters typically have considerable overlap between the red, green, and blue passbands, which can lead to considerable crosstalk when imaging dim autofluorescence light in the presence of intense reflected excitation light. Therefore, a separate filter 118 is provided to reduce the intensity of reflected excitation light to the same level as that of the autofluorescence light and, at the same time, pass autofluorescence light.

In this embodiment, the primary fluorescence and reference images are projected onto the same image sensor 103, but, because of the individual filters placed over each pixel, these different images are detected by separate sensor pixels. As a result, individual primary fluorescence and reference image signals can be produced by processor/controller 64 from the single CCD image signal.

Figure 7B:
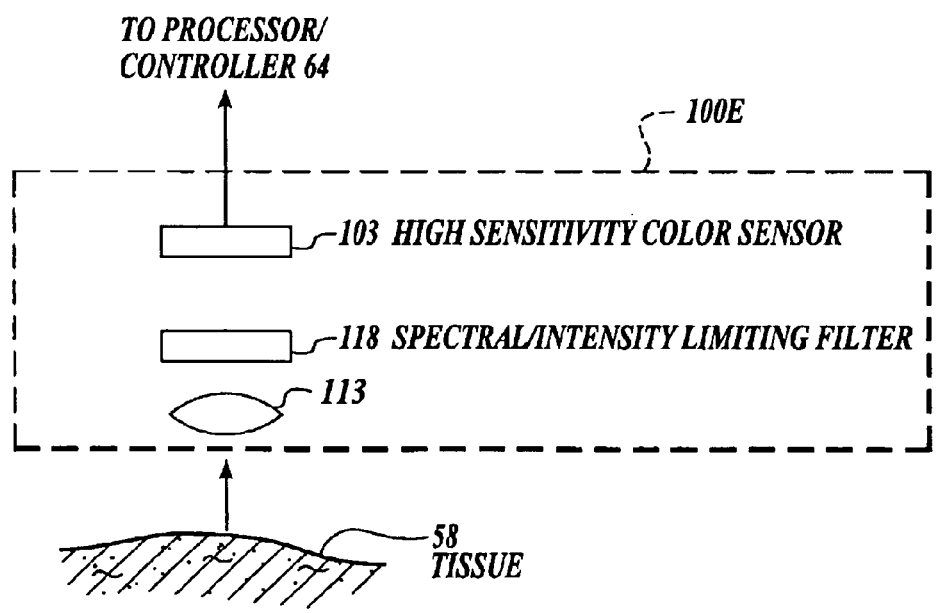

In FIG. 7A, light collimating optics 110 is positioned between the tissue 58 and filter 118 and imaging optics 112 is positioned immediately preceding the color image sensor 103. In an alternative optical configuration, camera 100E, as shown in FIG. 7B, eliminates the collimating optics 110 and imaging optics 112 and replaces them with a single imaging optics 113 located between the tissue 58 and filter 118. The advantage of this configuration is that all imaging is performed and controlled by the same imaging optics 113. The fact that filter 118 is located in a converging beam path must be considered in specifying that element and in the design of the imaging optics.

The operation of a system based on camera 100D of FIG. 7A or 100E of FIG. 7B will now be described. The cameras 100D and 100E are capable of operation in the color, fluorescence/fluorescence, and fluorescence/reflectance imaging modes. For a system based on camera 100D or 100E, a light source of the type shown in FIG. 2A, provides steady state output in each imaging mode. As described below, the light transmission specifications of the light source filters 76A, 76B, and 76C, the filter 1118, and the mosaic color filters integrated with the image sensor 103 are selected such that the intensity of the reflected light and fluorescence light at the color image sensor's active elements results in transduced image signals with good signal-to-noise characteristics and without significant saturation. At the same time these filters have appropriate light transmission specifications for excitation and imaging of the primary fluorescence and for color imaging. The filter transmission characteristics are chosen to provide the desired ratio of relative primary fluorescence to reference light intensity at the image sensor.

In the color imaging mode, the processor/controller 64 provides a control signal to the multimode light source 52 that it should be in white light mode. The light source selects and positions the appropriate optical filter 76A into the optical path between the arc lamp 70 and endoscope light guide 54. Given the presence of filter 118 in cameras 100D, 100E which have reduced transmission for excitation light at blue wavelengths, the light source filter 76A should incorporate reduced transmission at red and green wavelengths to obtain a balanced color image at image sensor 103 with the proper proportions of red, green, and blue components.

Image signals from the color low light sensor 103 are processed by processor/controller 64. Standard techniques are utilized to produce a color image from a single color sensor: the image signals from pixels having the same filter characteristics are interpolated by processor/controller 64 to produce an image signal, related to the pass band of each element of the mosaic filter (e.g. red, green, and blue), at every pixel location. The resulting multiple images, which when combined produce a color image, are encoded by processor/controller 64 as video signals. The color image is displayed by connecting the video signals to the appropriate inputs of color video monitor 66.

Processor/controller 64 also maintains the overall image brightness at a set level by monitoring the brightness of the image signal at each pixel and adjusting the intensity of the light source output and camera amplifier gains according to a programmed algorithm.

When switching to the fluorescence/fluorescence imaging mode, processor/controller 64 provides a control signal to the multi-mode light source 52 to indicate that it should be in fluorescence/fluorescence mode. The light source 52 moves light source filter 76B into position in the light beam. Filter 76B transmits excitation light and blocks the transmission of light at the green and red fluorescence detection wavelengths, as described below. The characteristics of light source fluorescence excitation filter 76B and excitation filter 118, along with the mosaic filter elements on the color sensor 103, are such that the intensity of blue light at the color sensor is less than the intensities of red and green autofluorescence at the sensor, and are such that the ratio of the intensity of red autofluorescence to the intensity of green autofluorescence at the color sensor 103 has the appropriate value for optimal differentiation between normal and abnormal tissue. The fluorescence images are processed, as previously described for color imaging, by processor/controller 64 to produce separate images corresponding to each of the pass bands of the mosaic filter (e.g. red, green, and blue). These separate images are encoded as video signals by processor/controller 64. A composite fluorescence/fluorescence image is displayed on the color video monitor 66 by applying the video signals from red and green pass bands of the mosaic filter to different color inputs of the monitor.

When switching to the fluorescence/reflectance imaging mode, processor/controller 64 provides a control signal to the multi-mode light source 52 to indicate that it should be in fluorescence/reflectance mode. The light source 52 moves light source filter 76C into position in the light beam. Filter 76C transmits both excitation light and reference light and blocks the transmission of light at fluorescence detection wavelengths, as described below. The characteristics of the light source filter 76C for fluorescence excitation and the reflectance illumination and the camera filter 118, along with the mosaic filter on the color sensor 103, as detailed below, are such that the intensity of reflected excitation light at the color sensor is comparable to the intensity of autofluorescence at the sensor, and should be such that the ratio of the intensity of autofluorescence to the intensity of reflected reference light at the color sensor 103 has the appropriate value. The fluorescence and reflectance images are processed, as previously described for color imaging, by processor/controller 64 to produce separate images corresponding to each of the pass bands of the mosaic filter (e.g. red, green, and blue). These separate images are encoded as video signals by processor/controller 64. A composite fluorescence/reflectance image is displayed on color video monitor 66 by applying the video signals from the appropriate mosaic filter pass bands (as discussed below) to different color inputs of the monitor.

As indicated above, the filters in the light source and camera should be optimized for the imaging mode of the camera, the type of tissue to be examined and/or the type of pre-cancerous tissue to be detected. Although all of the filters described below can be made to order using standard, commercially available components, the appropriate wavelength range of transmission and degree of blocking outside of the desired transmission range for the described fluorescence endoscopy images modes are important to the proper operation of the system. The importance of other issues in the specification of such filters such as the fluorescence properties of the filter materials and the proper use of anti-reflection coatings are taken to be understood.

As discussed above, the filters in the light source and camera should be optimized for the imaging mode of the camera, the type of tissue to be examined and/or the type of pre-cancerous tissue to be detected, based on in vivo spectroscopy measurements. The preferred filter characteristics for use in the fluorescence endoscopy video systems with a camera of the type shown in FIGS. 7A and 7B, operating in a fluorescence/reflectance imaging mode, or a fluorescence/fluorescence imaging mode, are shown in FIGS. 8A–8F. There are several possible configurations of fluorescence endoscopy video systems, operating in the fluorescence/reflectance imaging mode including green fluorescence with red reflectance, and red fluorescence with green reflectance and red or green fluorescence with blue reflectance. The particular configuration utilized depends on the target clinical organ and application. The filter characteristics will now be described for each of these four configurations.

FIGS. 8A–8B illustrate a preferred composition of the light transmitted by filters for a color imaging mode. FIG. 8A illustrates the composition of the light transmitted by the light source filter, such as filter 76A, which is used to produce light for color imaging. The spectral filter 118 remains in place during color imaging since there are no moving parts in the present camera embodiment. Accordingly, to achieve correct color rendition during color imaging it is necessary for the transmission of light source filter 76A to be modified, compared to the usual white light transmission for color imaging, such that the light received by the high sensitivity color sensor 103 is white when a white reflectance standard is viewed with the camera. Therefore, to balance the effect of spectral filter 118, the transmission of filter 76A in the red and green spectral bands must be less than the transmission in the blue, and the transmission of filter 76A in the blue must extend to a long enough wavelength that there is an overlap with the short wavelength region of appreciable transmission of filter 118. Filter 76A transmits light in the blue wavelength range from 370–480 nm or any subset of wavelengths in this range at the maximum possible transmission. The transmission of Filter 76A in the green and red wavelength range from 500 nm–750 nm, or any subsets of wavelengths in this range, is preferably reduced by at least a factor of ten compared to the transmission in the blue, in order to achieve a balanced color image at the high sensitivity color sensor 103, after taking into account the effect of filter 118.

FIG. 8B shows the composition of the light transmitted by the spectral filter 118, which is used for all imaging modes. In this configuration, the filter blocks the blue excitation light in the range 370–450 nm while transmitting red and green light in the wavelength range of 470–750 nm or any subsets of wavelengths in this range. When used in a fluorescence endoscopy video system in combination with the light source filter 76A described above, the filter characteristics are such that the intensity of light captured by high sensitivity color sensor 103 in the wavelength bands transmitted by the different regions of the sensor's mosaic filter are comparable, when a white reflectance standard is imaged. When used in a fluorescence endoscopy video system for fluorescence/fluorescence imaging in combination with the light source filter 76B described below, the filter characteristics are such that any light outside of the wavelength range of 470–750 nm (or any desired subset of wavelengths in this range) contributes no more than 0.1% to the light transmitted by the filter.

FIG. 8C illustrates the composition of the light transmitted by a filter, such as filter 76B, which is used to produce excitation light in the system light source. This filter transmits light in the wavelength range from 370–450 nm or any subset of wavelengths in this range. Of the light transmitted by this filter, preferably less than 0.001% is in the fluorescence imaging band from 470–750 nm (or whatever desired subsets of this range is within the transmission range of the primary and reference fluorescence wavelength bands defined by the transmission of the mosaic filter incorporated in the high sensitivity color sensor 103).

FIG. 8D illustrates the composition of the light transmitted by the light source filter, such as filter 76C, which is used to produce blue excitation light and red reference light for a green fluorescence and red reflectance imaging mode. This filter transmits light in the blue wavelength range from 370–450 nm, or any subset of wavelengths in this range. It also transmits light in the red wavelength range of 590–750 nm, or any subset of wavelengths in this range. The light transmitted in the red wavelength range (or subset of that range) is adjusted, as part of the system design, to be an appropriate fraction of the light transmitted in the blue wavelength range. This fraction is selected to meet the need to match the intensity of the reflected reference light projected on the color image sensor to the requirements of the sensor, at the same time as maintaining sufficient fluorescence excitation. Of the light transmitted by this filter, less than 0.001% is in the green wavelength range of 470–570 nm (or whatever desired subset of this range is specified as the transmission range of the primary fluorescence wavelength band).

FIG. 8E illustrates the composition of the light transmitted by a light source filter which is used to produce excitation light such as filter 76C described above for a red fluorescence and green reflectance imaging mode. This filter transmits light in the blue wavelength range from 370–450 nm or any subset of wavelengths in this range. It also transmits light in the green wavelength range of 470–570 nm or any subset of wavelengths in this range. The light transmitted in the green wavelength range (or subset of that range) is adjusted, as part of the system design, to be an appropriate fraction of the light transmitted in the blue wavelength range. This fraction is selected to meet the need to match the intensity of the reflected reference light projected on the color image sensor to the requirements of the sensor, at the same time as maintaining sufficient fluorescence excitation. Of the light transmitted by this filter, less than 0.001% is in the red fluorescence imaging wavelength range of 590–750 nm (or whatever desired subset of this range is specified as the transmission range of the primary fluorescence wavelength band).

FIG. 8F illustrates the composition of the light transmitted by a light source filter which is used to produce excitation light such as filter 76C described above for a red or green fluorescence and blue reflectance imaging mode. This filter transmits light in the blue wavelength range from 370–470 nm or any subset of wavelengths in this range. The light transmitted in the 450–470 nm wavelength range (or subset of that range) is adjusted, as part of the system design, to meet the need to match the intensity of the reflected reference light projected on the color image sensor to the requirements of the sensor and to provide the appropriate ratio of reference reflected light to fluorescence light, at the same time as maintaining sufficient fluorescence excitation.

Of the light transmitted by this filter, less than 0.001% is in the fluorescence imaging wavelength range of 490–750 nm (or whatever desired subset of this range is specified as the transmission range of the primary fluorescence wavelength band).

The fluorescence endoscopy video systems described in the above embodiments have been optimized for imaging endogenous tissue fluorescence. They are not limited to this application, however, and may also be used for photodynamic diagnosis (PDD) applications. As mentioned above, PDD applications utilize photo-active drugs that preferentially accumulate in tissues suspicious for early cancer. Since effective versions of such drugs are currently in development stages, this invention does not specify the filter characteristics that are optimized for such drugs. With the appropriate light source and camera filter combinations, however, a fluorescence endoscopy video system operating in either fluorescence/fluorescence or fluorescence/reflectance imaging mode as described herein may be used to image the fluorescence from such drugs.

As will be appreciated, each of the embodiments of a camera for a fluorescence endoscopy video system described above, due to their simplicity, naturally lend themselves to miniaturization and implementation in a fluorescence video endoscope, with the camera being incorporated into the insertion portion of the endoscope. The cameras can be utilized for both color imaging and fluorescence imaging, and in their most compact form contain no moving parts.

What is claimed is:

1. A color and fluorescence endoscopy video system including:
    an endoscope for directing the light from a multi-mode light source into a patient to illuminate a tissue sample and to collect reflected light or fluorescence light produced by the tissue;
    a camera positioned to receive the light collected by the endoscope to produce color or fluorescence images, the camera including:
       a low light color image sensor having integrated filters with color output;
       one or more filters positioned in front of the low light color image sensor for selectively blocking light with wavelengths below 450 nm and transmitting visible light with wavelengths greater than 470 nm; and
       one or more optical imaging components that project images onto the low light color image sensor;
    an image processor/controller that receives image signals from the low light color image sensor and combines and interpolates image signals from pixels having filters with the same integrated filter characteristics to fluorescence or reflectance light and then encodes the images as video signals;
    a multi-mode light source for producing light for color imaging and/or for fluorescence excitation and/or for fluorescence excitation with reference reflectance, including a filter selectively positioned in the light path of the light source for producing light for color imaging that simultaneously transmits blue light at wavelengths less than 480 nm and amounts of green and red light, wherein the amounts of green and red light transmitted are adjusted to be a fraction of the transmitted blue light, such that, when reflected from a gray surface, the intensity of the green and red light projected onto the low light color image sensor matches the intensity of blue light also projected onto the low light color image sensor in such a way that the resulting color images are white balanced; and
    a color video monitor for displaying superimposed video images from the pixels of the low light color image sensor.

2. The system of claim 1, wherein the camera is attached to the portion of the endoscope that remains outside of the body.

3. The system of claim 1, wherein the camera is built into the insertion portion of the endoscope.

4. The system of claim 2 or 3, further comprising a light source filter selectively positioned in the light path of the light source for producing light for fluorescence excitation and reference reflection that simultaneously transmits the fluorescence excitation light at wavelengths less than 450 nm and an amount of reference reflectance light not in a fluorescence detection wavelength band, wherein the amount of reference reflectance light transmitted is a fraction of the fluorescence excitation light, such that the intensity of the reflected reference light projected onto the low light color image sensor approximately matches the intensity of fluorescence light also projected onto the low light color image sensor, the light source filter also blocking light from the light source at wavelengths in the fluorescence detection wavelength band such that the fluorescence light received by the low light color image sensor is substantially composed of light resulting from tissue fluorescence and minimally composed of light originating from the light source.

5. The system of claim 4, wherein the fluorescence light, transmitted by the one or more filters positioned in front of the low light color image sensor, is green light.

6. The system of claim 5, wherein the reference reflectance light, not in the detected fluorescence band, transmitted by the light source filter is red light.

7. The system of claim 4, wherein the fluorescence light, transmitted by the one or more filters positioned in front of the low light color image sensor, is red light.

8. The system of claim 6, wherein the image processor/controller produces a composite fluorescence/reflectance image comprising an image created from green fluorescence light and an image created from red reflectance light that are superimposed and displayed in different colors on a color video monitor.

9. The system of claim 7, wherein the reference reflectance light, not in the detected fluorescence band, transmitted by the light source filter is green light.

10. The system of claim 7, wherein the image processor/controller produces a composite fluorescence/reflectance image comprising an image created from red fluorescence light and an image created from green reflectance light that are superimposed and displayed in different colors on a color video monitor.

11. The system claim 2 or 3, further comprising a filter positioned in the light path of the light source that transmits fluorescence excitation light at wavelengths less than 450 nm and blocks light at visible wavelengths longer than 450 nm, from reaching the low light color image sensor to the extent that the light received by the low light color image sensor is substantially composed of light resulting from tissue fluorescence and minimally composed of light originating from the light source.

12. The system of claim 11, wherein the image processor/controller produces a composite fluorescence/reflectance image comprising an image created from green fluorescence light and an image created from red fluorescence light that are superimposed and displayed in different colors on a color video monitor.

13. The system of claim 1 wherein the image processor/controller produces a composite color image comprising red reflectance light, green reflectance light, and blue reflectance light images that are superimposed and displayed respectively on red, green, and blue channels of a color video monitor, when the light source filter for producing light for color imaging is inserted into the light path of the light source.

14. A color and fluorescence endoscopy video system including:
   an endoscope for directing the light from a multi-mode light source into a patient to illuminate a tissue sample and to collect reflected light or fluorescence light produced by the tissue;
   a camera positioned to receive the light collected by the endoscope to produce color or fluorescence images, the camera including:
      a low light color image sensor having integrated filters with color output;
      one or more filters positioned in front of the low light color image sensor for selectively blocking light with wavelengths below 450 nm and transmitting visible light with wavelengths greater than 470 nm; and
      one or more optical imaging components that project images onto the low light color image sensor;
   an image processor/controller that receives image signals from the low light color image sensor and combines and interpolates image signals from pixels having filters with the same integrated filter characteristics to fluorescence or reflectance light and then encodes the images as video signals;
   a multi-mode light source for producing light for color imaging and/or for fluorescence excitation and/or for fluorescence excitation with reference reflectance, including a light source filter selectively positioned in the light path of the light source that simultaneously transmits the fluorescence excitation light at wavelengths less than 450 nm and an amount of reference reflectance light not in a fluorescence detection wavelength band, wherein the amount of reference reflectance light transmitted is a fraction of the fluorescence excitation light, such that the intensity of the reflected reference light projected onto the low light color image sensor is approximately matched to the intensity of fluorescence light also projected onto the low light color image sensor, the light source filter also blocking light from the light source at wavelengths in the fluorescence detection wavelength band such that the fluorescence light received by the low light color image sensor is substantially composed of light resulting from tissue fluorescence and minimally composed of light originating from the light source; and
   a color video monitor for displaying superimposed video images from the pixels of the low light color image sensor.

15. The system of claim 14, wherein the camera is attached to the portion of the endoscope that remains outside of the body.

16. The system of claim 14, wherein the camera is built into the insertion portion of the endoscope.

17. The system of claim 15 or 16, further comprising a filter selectively positioned in the light path of the light source that transmits fluorescence excitation light at wavelengths less than 450 nm and blocks light at visible wavelengths longer than 450 nm, from reaching the low light color image sensor to the extent that the light received by the low light color image sensor is substantially composed of light resulting from tissue fluorescence and minimally composed of light originating from the light source.

18. The system of claim 17, wherein the image processor/controller produces a composite fluorescence/reflectance image comprising an image created from green fluorescence light and an image created from red fluorescence light that are superimposed and displayed in different colors on a color video monitor.

19. The system of claim 15 or 16, further comprising a filter selectively positioned in the light path of the light source for producing light for color imaging that simultaneously transmits blue light at wavelengths less than 480 nm and amounts of green and red light, wherein the amounts of red and green light transmitted are adjusted to be a fraction of the transmitted blue light, such that, when reflected from a gray surface, the intensity of the green and red light projected onto the low light color image sensor matches the intensity of blue light also projected onto the low light color image sensor in such a way that the resulting color images are white balanced.

20. The system of claim 14, wherein the fluorescence light, transmitted by the one or more filters positioned in front of the low light color image sensor, is green light.

21. The system of claim 20, wherein the reference reflectance light, not in the detected fluorescence band, transmitted by the light source filter is red light.

22. The system of claim 21, wherein the image processor/controller produces a composite fluorescence/reflectance image comprising an image created from green fluorescence light and an image created from red reflectance light that are superimposed and displayed in different colors on a color video monitor.

23. The system of claim 14, wherein the fluorescence light, transmitted by the one or more filters positioned in front of the low light color image sensor, is red light.

24. The system of claim 23, wherein the reference reflectance light, not in the detected fluorescence band, transmitted by the light source filter is green light.

25. The system of claim 24, wherein the image processor/controller produces a composite fluorescence/reflectance image comprising an image created from red fluorescence light and an image created from green reflectance light that are superimposed and displayed in different colors on a color video monitor.

26. The system of claim 14, wherein the image processor/controller produces a composite color image comprising red reflectance light, green reflectance light, and blue reflectance light images that are superimposed and displayed respectively on red, green, and blue channels of a color video monitor.

* * * * *

UNITED STATES PATENT AND TRADEMARK OFFICE
CERTIFICATE OF CORRECTION

PATENT NO. : 6,899,675 B2
DATED : May 31, 2005
INVENTOR(S) : R.W. Cline et al.

It is certified that error appears in the above-identified patent and that said Letters Patent is hereby corrected as shown below:

Title page,
Item [56], References Cited, U.S. PATENT DOCUMENTS, "Wägnieres et al." should read -- Wagnieres et al. --.
FOREIGN PATENT DOCUMENTS, insert in appropriate order
-- FR   2 671 405      7/1992 --.

Column 16,
Line 51, "The system claim 2 or 3," should read -- The system of claim 2 or 3, --.

Signed and Sealed this

Eleventh Day of October, 2005

JON W. DUDAS
*Director of the United States Patent and Trademark Office*